United States Patent [19]

Almen et al.

[11] Patent Number: 5,366,722
[45] Date of Patent: Nov. 22, 1994

[54] CONTRAST MEDIA COMPRISING A NON-IONIC CONTRAST AGENT AND SODIUM IONS

[75] Inventors: Torsten Almen, Malmo; Laars BÅÅth, Malmö, both of Sweden; Audun Oksendal, Oslo, Norway

[73] Assignee: Nycomed Imaging AS, Oslo, Norway

[21] Appl. No.: 156,998

[22] PCT Filed: Mar. 9, 1990

[86] PCT No.: PCT/EP90/00393
§ 371 Date: Sep. 24, 1991
§ 102(e) Date: Sep. 24, 1991

[87] PCT Pub. No.: WO90/11094
PCT Pub. Date: Oct. 4, 1990

Related U.S. Application Data

[63] Continuation of Ser. No. 761,738, Sep. 24, 1991, abandoned.

[30] Foreign Application Priority Data

Mar. 17, 1989 [GB] United Kingdom ............ 89 06130.3

[51] Int. Cl.$^5$ ...................... A61B 5/055; A61K 49/04
[52] U.S. Cl. ............................ 424/4; 424/5; 424/9; 424/722; 514/576; 514/922
[58] Field of Search ............ 424/4, 5, 9, 722; 514/576, 922

[56] References Cited

U.S. PATENT DOCUMENTS

| | | | |
|---|---|---|---|
| 4,283,381 | 8/1981 | Speck et al. | 424/5 |
| 4,364,921 | 12/1982 | Speck et al. | 424/5 |
| 4,426,371 | 1/1984 | Pfeiffer et al. | 424/5 |
| 4,649,050 | 3/1987 | Veech | 424/601 |
| 4,663,166 | 5/1987 | Veech | 424/663 |
| 4,963,344 | 10/1990 | Gries et al. | 424/9 |
| 5,011,925 | 4/1991 | Rajagopalan et al. | 544/58.1 |

FOREIGN PATENT DOCUMENTS

11336/88 11/1988 Australia .

OTHER PUBLICATIONS

Almen et al., *Acta Radiologica Diagnosis*, 17 (1976), 439–448.
Morris, *Investigative Radiology*, 23, 205–208, 1988.
Ralston, *Investigative Radiology*, 23, S140–143, 1988.
Zucker, *Investigative Radiology*, 23, S340–345, 1988.
Simon et al., *AJR*, 114, 810–816, 1972.
Piao et al., *Investigative Radiology*, 23, 466–470, 1988.
Kozeny et al., *Am. Heart J.*, 109, 290 (1984).

*Primary Examiner*—Gary E. Hollinden
*Attorney, Agent, or Firm*—Bacon & Thomas

[57] ABSTRACT

The invention relates to improved contrast media containing non-ionic contrast agents, e.g. non-ionic iodinated X-ray contrast agents, the improvement being achieved by incorporation of sodium at 20–60 mM/l.

10 Claims, 2 Drawing Sheets

○ Iopentol
● Iohexol

CONTRAST MEDIA COMPRISING A NON-IONIC CONTRAST AGENT AND SODIUM IONS

This application is a continuation of U.S. application Ser. No. 07/761,738, filed Sep. 24, 1991 now abandoned.

This invention relates to contrast media, in particular non-ionic X-ray contrast media.

Contrast media may be administered in medical imaging procedures, for example X-ray, magnetic resonance and ultrasound imaging, to enhance the image contrast in images of a subject, generally a human or non-human animal body. The resulting enhanced contrast enables different organs, tissue types or body compartments to be more clearly observed or identified. In X-ray imaging the contrast media function by modifying the X-ray absorption characteristics of the body sites in which they distribute; magnetic resonance contrast media generally function by modifying the characteristic relaxation times $T_1$ and $T_2$ of the nuclei, generally water protons, from the resonance signals of which the images are generated; and ultrasound contrast media function by modifying the speed of sound or density in the body sites into which they distribute.

Clearly however the utility of a material as a contrast medium is governed to a large extent by its toxicity and any other adverse effects it may have on the subject to which it is administered. Since such media are conventionally used for diagnostic purposes rather than to achieve a direct therapeutic effect, when developing new contrast media there is a general desire to develop media having as little as possible an effect on the various biological mechanisms of the cells or the body as this will generally lead to lower animal toxicity and lower adverse clinical effects.

The toxicity and adverse effects of a contrast medium are contributed to by the components of the medium, e.g. the solvent or carrier as well as the contrast agent and its components (e.g. ions where it is ionic) and metabolites.

The following major contributing factors to contrast media toxicity and adverse effects have been identified:
the chemotoxicity of the contrast agent,
the osmolality of the contrast medium, and
the ionic composition (or lack thereof) of the contrast medium.

Thus in coronary angiography, for example, injection into the circulatory system of contrast media has been associated with several serious effects on cardiac function, efforts sufficiently severe as to place limitations on the use in angiography of certain contrast media.

In this procedure, for a short period of time a bolus of contrast medium rather than blood flows through the circulatory system and differences in the chemical and physicochemical nature of the contrast medium and the blood that it temporarily replaces can give rise to undesirable effects, e.g. arrhythmias, QT-prolongation, and, especially, occurrence of ventricular fibrillation and reduction in cardiac contractile force.

Contrast media generally fall into two groups, the so-called ionic and non-ionic contrast media. In these the contrast agent, in solution, is respectively in ionic form or in molecular or particulate form.

Most conventional X-ray contrast media contain as the contrast agent an iodine containing material. (Iodine which has a relatively high atomic weight accordingly has a relatively large cross-section to X-rays).

Thus the contrast medium used in angiography may have an iodine concentration as high as 250–450 mg I/ml and at that concentration range ionic contrast agents of ratio 1.5 (such as diatrizoate, iothalamate, ioxithalamate, iodamide and metrizoate) have an osmolality 5 to 9 times that of normal human plasma, ionic contrast agents of ratio 3 (e.g. ioxaglate) or non-ionic contrast agents of ratio 3 (e.g. metrizamide, iopromide, iopentol, iopamidol and iohexol) have an osmolality about a half as large, and non-ionic contrast agents of ratio 6 (e.g. iotrolan and iodixanol) have an osmolality about quarter that of the ratio 1.5 ionic contrast agents at the same iodine concentration. Ratio 6 non-ionic contrast agents may even be used at iodine concentrations where they are hypotonic so that normal plasma ions and other conventional osmoactive agents may be added to produce isotonicity with normal plasma. By "ratio 3" in the above paragraph it is meant that the ratio of iodine atoms to contrast agent particles (i.e. ions or molecules) is 3. Ratio 1.5 ionic and ratio 3 non-ionic contrast agents generally contain one triiodophenyl moiety and ratio 3 ionic and ratio 6 non-ionic contrast agents generally contain two triiodophenyl moieties.

Thus, for the most part, at iodine concentrations of for example 250 mg I/ml, X-ray contrast media will be hypertonic. This hypertonicity causes osmotic effects such as the draining out of water from red-blood cells, endothelial cells, and heart and blood vessel muscle cells. Loss of water makes red blood cells stiff and hypertonicity, chemotoxicity and non-optimal ionic make-up separately or together reduce the contractile force of the muscle cells and cause dilation of small blood vessels and a resultant decrease in blood pressure.

There is thus a general reluctance to add ions to isotonic or already hypertonic contrast media as this will result in or will increase hypertonicity and thus will increase osmotic side effects.

However, as mentioned above, an important contributory factor to the toxicity and adverse effects of contrast media is the ionic make-up of, or the total lack of ions in, the contrast medium. Of necessity, ionic contrast media contain counterions, generally countercations, to the iodinated ions which conventionally are anions. There has been a great deal of research into the cationic composition of these ionic contrast media and although commercially the cations are often sodium ($Na^+$) and/or meglumine ($Meg^+$), plasma ions such as calcium, potassium and magnesium may also be included.

Thus while it is generally accepted that cardiac muscle contractile force reduction is made more severe by increasing sodium ion concentration, the results of Almen (see Acta Radiologica Diagnosis 17:439–448 (1976)) on a bat wing vein model for the determination of the effect of contrast media on smooth muscle contractility suggest that the absence of normal plasma ion concentrations of normal plasma cations (i.e. sodium, potassium, magnesium and calcium) adversely affects muscle contractivity. The results of Simon et. al. AJR 114:810–816 (1972) for diatrizoate based ionic contrast media strongly suggest that there is a danger in coronary angiography of ventricular fibrillation where the sodium ion concentration in the contrast medium falls well beneath normal plasma levels, e.g. below 70 mM/l. Further research has in general suggested that ventricular fibrillation occurs when sodium ion concentrations in contrast media fall below about 3.2 to 2.6 mM/liter (see Morris in Investigative Radiology 23: S127–S129

(1988)). Indeed, there has been concern that the incidence of ventricular fibrillation with non-ionic contrast media might be unacceptably high (see Piao et. al. Investigative Radiology 23: 466–470 (1988)).

By adding calcium and magnesium ions to ionic contrast media containing sodium and meglumine cations, it has also been found that effects on the blood brain barrier can be decreased and that animal acute intravenous toxicity can also be reduced.

However, while investigations have shown that the addition of plasma ions to X-ray contrast media may modify the biological effects of such media, it is recognized, as mentioned above, that any addition of ions to a hypertonic composition will increase hypertonicity and as a result will increase osmotic effects. Consequently while the literature shows that the danger of ventricular fibrillation with non-ionic contrast media may be reduced by incorporation within such media of low sodium concentrations and that undesirable reductions in muscle cell contractile force may be decreased by inclusion of normal plasma concentrations of normal plasma cations, the literature does not show a consensus within the art as to the optimal cation content for contrast media.

Earlier research has also shown that the presence of sodium ions in contrast media results in reduced red blood cell aggregate formation in human blood and also in decreased erythrocyte aggregation. Zucker et. al. (see Investigative Radiology 23: S340–S345 (1988)) have consequently suggested that the non-ionic X-ray contrast medium iohexol might be formulated to contain sodium, added as NaCl, at a concentration of 15 mM/liter to decrease red blood cell aggregation without simultaneously causing an unacceptably large increase in osmolality.

The teachings of the literature are thus somewhat inconsistant and contradictory regarding optimal cation make-up for contrast media. From the point of view of osmotoxicity, addition of cations is contraindicated where it would result in hypertonicity or in increased hypertonicity, yet from the point of view of avoidance of ventricular fibrillation inclusion of at least about 3.2 mM/liter of sodium is thought to be desirable. Moreover, from the point of view of avoidance of undue reduction in muscle contractile force, the work of Almen mentioned above points towards the inclusion of normal plasma concentrations of normal plasma ions while work by Kozeny et. al. (see Am. Heart J. 109:290 (1984)) suggests that increasing the sodium ion concentration in a contrast medium may increase the contractile force reducing effect, the negative inotropic effect, of that medium.

We have now surprisingly found that adverse effects of non-ionic contrast media can be reduced by the inclusion of sodium ions in the media within the relatively narrow concentration range of from greater than 20 to 60 mM Na/liter, particularly 25 to 40 mM Na/liter, especially 26 to 36 mM Na/liter, and especially preferably about 27 to 30 mM Na/liter.

The present invention lies in part in the surprising finding that sodium ion addition in relatively low concentrations results in a decrease in the contractile force reducing effect of the contrast medium as compared with the same medium free of sodium ions, although higher sodium ion concentrations, as already known, result in increasing contractile force reductions. The invention also results in part from the finding that the various forms of aggregation of red blood cells are optimized within the sodium ion concentration ranges specified above. Within these ranges, the formation of rouleaux, which are also known as two-dimensional aggregates and which may be considered to be an indicator of normal red blood cell aggregability, is optimized while at lower sodium ion concentrations red blood cell aggregate formation is increased and at higher sodium ion concentrations echinocyte formation is increased. Moreover, sodium ion concentrations in the ranges specified above are sufficient to avoid the risks of ventricular fibrillation encountered at low sodium ion concentrations.

Thus in one aspect, the invention provides a contrast medium comprising a non-ionic contrast agent, preferably an iodinated X-ray contrast agent, in a physiologically tolerable aqueous carrier medium, characterized in that said contrast medium has a sodium ion concentration of from greater than 20 (for example 20.1 or above) to 60 mM/liter, preferably 25 to 40 mM/liter, especially preferably 26 to 36 mM/liter and most especially preferably 27 to 30 mM/liter, with the proviso that where said agent is loversol said contrast medium contains sodium ions in the concentration range 26 to 36 mM/liter, preferably 27 to 34 mM/liter.

In the foregoing paragraph a reference is made to the non-ionic X-ray contrast agent ioversol; this reference is made in view of the disclosure by Ralston et. al. (see Investigative Radiology 23; S140–S143 (1988)) of trial solutions comprising ioversol and 12.4, 25.6, 38.5, 77 and 144 mM/liter sodium ions. Ralston et. al. investigated the effect of sodium on the potential for ventricular fibrillation of ioversol and found that the addition of sodium to ioversol generally reduced the propensity for spontaneous ventricular fibrillation in the canine model. The results of Ralston et. al. did not however suggest an optimal sodium ion concentration in the range 20 to 60 mM/liter, let alone an optimum concentration in the more preferred range of 27 to 30 mM/liter.

In effect the present invention lies in the determination that the negative effects of enhanced osmolality resultant on providing a non-ionic X-ray contrast medium with a sodium ion concentration of from greater than 20 up to 60 mM/liter are outweighed by the resultant positive factors:

the occurrence of ventricular fibrillation is less than at lower sodium concentrations;
the reduction in contractile force is less than at either higher or lower sodium ion concentrations;
red blood cell aggregate formation is less than at lower sodium concentrations;
echinocyte formation is less than at higher sodium ion concentrations; and
rouleaux formation is greater than at either lower or higher sodium ion concentrations.

The present invention is especially applicable to X-ray contrast media containing contrast agents of ratio 3, such as for example those mentioned above.

Figure 1:
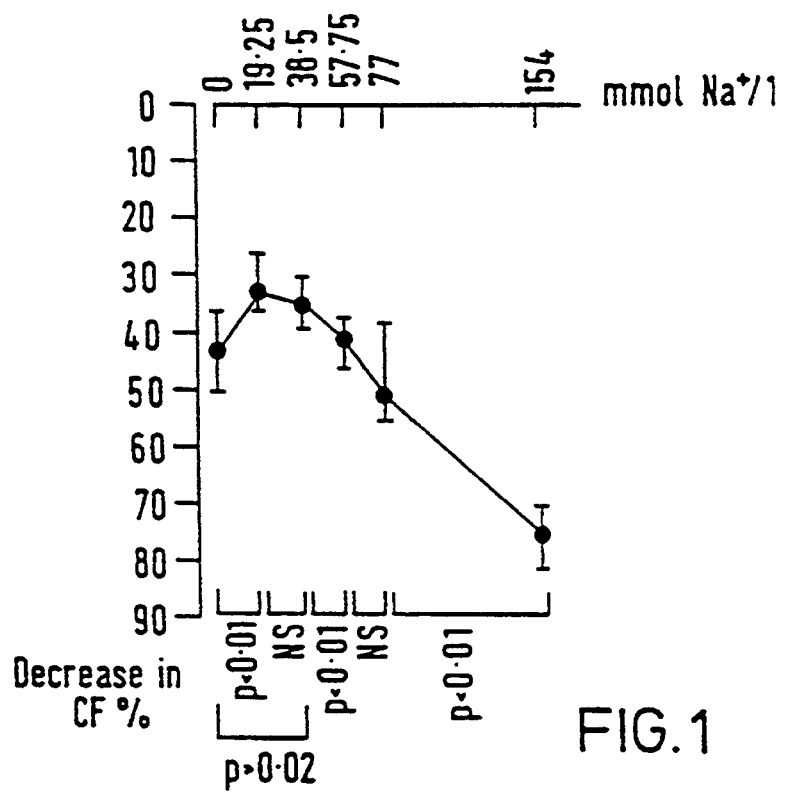
FIG. 1 depicts the decrease in contractile force following infusion of 15 hearts with 150 mg I/ml iohexol and sodium ions at varying concentrations.

The contrast media of the invention, where they contain iodinated contrast agents, will particularly preferably contain such agents at concentrations of at least 100 mgI/ml, eg 150-500 mgI/ml, especially preferably 200-350 mgI/ml. Moreover, while the general constraint that the deviation from isotonicity should if possible be minimized applies, it is generally preferable that the osmolality of the contrast media of the invention be less than 1 osm/kg $H_2O$, especially preferably 850 mosm/kg $H_2O$ or less.

The sodium ions may conveniently be incorporated within the contrast media of the invention in the form of sodium salts with physiologically tolerable counterions. Particularly suitable counterions include plasma anions such as chloride, phosphate and hydrogencarbonate ions. However, the sodium may alternatively be incorporated, at least in part, in the form of a salt of a physiologically tolerable chelating agent, e.g. sodium edetate or calcium disodium edetate (for example to contribute 0.5 to 1.5 mM Na/liter to the overall sodium ion concentration without affecting the calcium balance in the plasma). Besides sodium ions, other physiologically tolerable cations may be incorporated within the contrast media of the invention. The contrast media of the invention may therefore conveniently be produced by the addition to existing contrast media of sodium salts, either as solids or already in solution, or of sodium-containing salt mixtures or solutions thereof.

Viewed from a further aspect the invention thus also provides a process for the preparation of a contrast medium, said process comprising admixing, optionally after dispersion in a physiologically tolerable aqueous carrier medium, a non-ionic contrast agent and a source of sodium ions and if necessary diluting the resulting mixture whereby to produce a contrast medium having a sodium ion concentration of greater than 20 mM/liter up to 60 mM/liter, or 26 to 36 mM/liter where said contrast agent is Ioversol.

The contrast media of the invention are particularly suited for intravascular administration and especially for use in cardiac imaging. Thus in a further aspect the present invention provides the use of a non-ionic contrast agent and of a physiologically tolerable sodium salt or a solution thereof in a physiologically tolerable solvent, e.g. water for injections, for the manufacture of a contrast medium according to the invention for use in cardiac imaging.

It is to be noted that from preliminary results it is considered at present that for iodixanol or iohexanol containing contrast media according to the invention the inclusion of 0.3 to 0.6 mM $Ca^{2+}$/liter or about 0.2 mM$Ca^{2+}$/liter respectively may further enhance the improvement in properties of the contrast media. Similarly, experimental results show oxygenation, e.g. oxygen saturation, of the media also to be effective in improving their properties.

Figure 2:
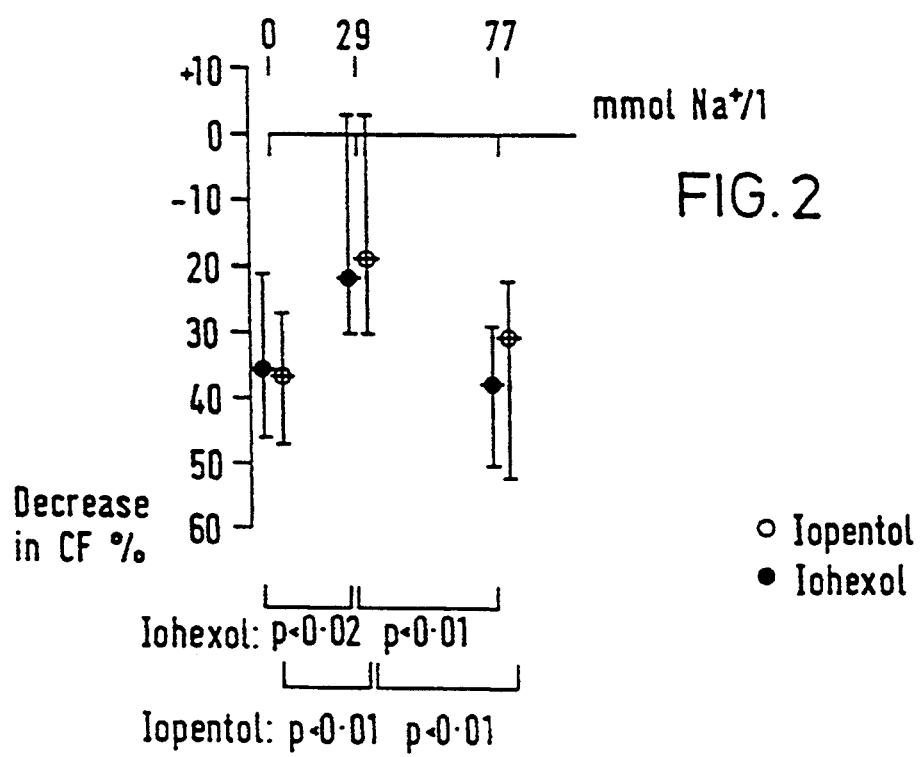
FIG. 2 depicts the decrease in contractile force following infusion of 15 hearts with 300 mg I/ml iohexol or iopentol and sodium ions at varying concentrations.
Figure 3:
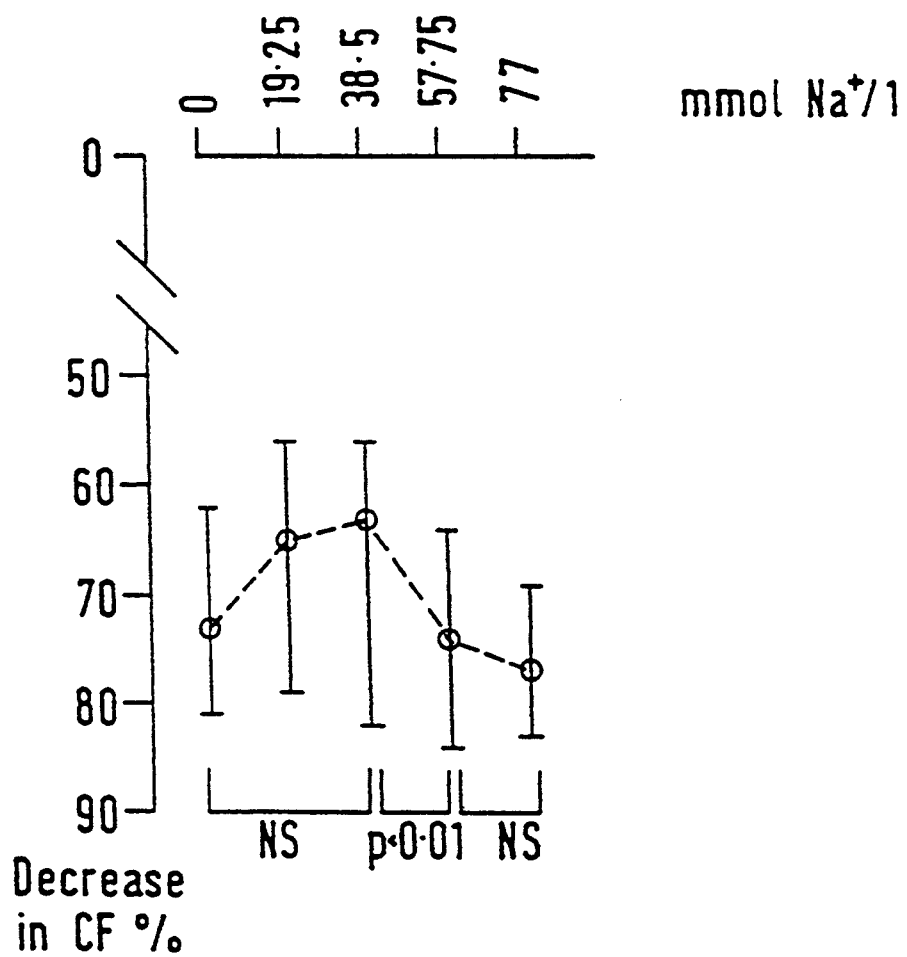
FIG. 3 depicts the decrease in contractile force following infusion of 13 hearts with 350 mg I/ml iohexol and sodium ions at varying concentrations.

The present invention will now be described further with reference the following non-limiting Examples and to the accompanying drawings, in which:

FIGS. 1 to 3 are graphs illustrating the reduction in contractile force of the rabbit heart with sodium ion concentration following infusion of iohexol or iopentol with or without added sodium.

INVESTIGATION OF THE EFFECT ON CARDIAC CONTRACTILE FORCE OF SODIUM ADDITION TO NON-IONIC CONTRAST MEDIA

Rabbit hearts were donated by rabbits of both sexes (weight 2.2-4.2 kg) which were anesthetized intravenously with pentobarbitone (Mebumal Vet. ACO) and heparinized (Heparin, Kabi Vitrum, 1000 IU/kg). The heart, lungs and aorta were quickly removed and placed in a bowl containing oxygenated Krebs' solution with added glucose 11.0 mmol/l and sucrose 12.0 mmol/l, either at 4° C. or at 37° C. The heart was then mounted on a polyethylene catheter according to the Langendorff technique at a pressure of 90 cm $H_2O$. The heart was per(used with Krebs' solution saturated with a mixture of 95% oxygen and 5% carbon dioxide at 37° C.

The perfusion fluid was delivered from a container through two parallel plastic tubes connected with a T-valve to the aortic catheter just above its entrance into the ascending aorta. The T-valve was turned so that the connection between one of the plastic tubes and the aortic catheter was closed. Test solution was then injected into the closed tube while perfusion fluid was simultaneously flowing through the other tube. Then the T-valve was turned so that the flow of perfusion fluid to the aortic catheter was stopped and the flow of test solution was started.

A strain gauge (Dept. of Medical Technology Malmgö General Hospital) was sutured to the wall of the left ventricle for measurement of the contractile force of the myocardium. A mingograph 800 (Elema Schöander) was used for recordings. Contractile force was measured as minimum contractile force after contrast medium infusion as a percentage of contractile force immediately before each infusion.

The following investigations were performed:

1: Iohexol (300 mg I/ml) was diluted with stock solutions of NaCl to reach an iodine concentration of 150 mg I/ml. The stock solutions contained NaCl in concentrations such that the final contrast media contained 0, 19.25, 38.5, 57.75, 77 or 154 mM Na/liter. Each of 15 hearts was infused with 7.5 ml of each of the 6 contrast media in random order, i.e. a total of 90 infusions.

2: To iohexol (300 mg I/ml) and iopentol (300 mg I/ml) 0, 29 or 77 mM Na/liter were added as solid NaCl. Each of 15 hearts was infused with 5 ml of each of the 6 contrast media in random order, i.e. a total of 90 infusions.

3: To Iopentel (350 mg I/ml) 0, 19.25, 38.5, 57.75 or 77 mM Na/liter were added as solid NaCl. Each of 15 hearts was infused with 5 ml of each of the 5 contrast media in random order.

The contrast media were infused at 37° C. at 10 minute intervals.

Wilcoxon signed rank test was used for statistical analysis.

A p-value less than 0.05 was considered significant.

The decrease in contractile force (the median decrease and interquartile range) observed following infusion of 15 hearts with 7.5 ml iohexol (150 mg I/ml) with 0, 19.25, 38.5, 57.75, 77 and 154 mM/liter sodium ions (added as sodium chloride) is shown in FIG. 1. All the contrast media caused decreases in contractile force, but this decrease surprisingly is reduced at sodium ion concentrations in the range of about 20 to 60 mM/liter.

The decrease in contractile force (again the median decrease and interquartile range) following infusion of 15 hearts with iohexol (300 mg I/ml) or Iopentel (300 mg I/ml) with 0, 29 and 77 mM/liter sodium ions (added as sodium chloride) is shown in FIG. 2. A significantly smaller decrease in contractile force was caused by the media containing 29 mM/liter sodium ions than by those media containing 0 or 77 mM/liter sodium.

The decrease in contractile force (median decrease and interquartile range) following infusion of 13 hearts with 5 ml iopentol (350 mg I/ml) with 0, 19.25, 38.5, 57.75 and 77 mM/liter sodium ions added as sodium chloride is shown in FIG. 3.

INVESTIGATION OF THE EFFECT ON BLOOD CELL AGGREGATION OF SODIUM ADDITION TO CONTRAST MEDIA

The effect on blood cell aggregation of incorporation of sodium ions within the contrast media of the invention was investigated as follows: one part of human blood was added to 3 parts of a contrast medium comprising iohexol (300 mg I/ml) and 0, 18.8, 23.4, 28.1, 32.8 or 37.5 mM/liter sodium (added as sodium chloride). This was done for blood from 10 to 29 human volunteers. The degrees of cell aggregation and rouleaux formation were determined and the results for the different sodium ion concentrations are presented in Tables 1 to 3 below. As far as red blood cell aggregates are concerned, these were catagorized as (a) few aggregates (where 0 to 20% of the red blood cells were in aggregates), (b) intermediate numbers of aggregates (where 20 to 70% of the red blood cells were in aggregates), and (c) many aggregates (where more than 70% of the red blood cells were in aggregates).

TABLE 1

Human red blood cell aggregation within 2 minutes following addition of contrast media containing iohexol (300 mg I/ml) and 0 to 37.5 mM/liter sodium ions.

| Na ion concentration (mM/l) | Aggregates | | | | Rouleaux | All cells separate |
|---|---|---|---|---|---|---|
| | a | b | c | Total | | |
| 0 | | | 15 | 15 | | |
| 18.8 | 11 | 4 | | 15 | 1 | |
| 23.4 | 7 | | | 7 | 7 | 1 |
| 28.1 | 1 | | | 1 | 9 | 5 |
| 32.8 | | | | | | 15 |
| 37.5 | | | | | | 15 |

Sample size = 15. The blood of all 15 human volunteers was tested at each sodium concentration.

TABLE 2

Effect on human red blood cell aggregation within 2 minutes of the addition of a contrast medium comprising iohexol (300 mg I/ml) and 0 to 150 mM/liter sodium ions (added as sodium chloride).

| Na ion concentration (mM/l) | N | Aggregates | | | | Rouleaux | All cells separate |
|---|---|---|---|---|---|---|---|
| | | a | b | c | Total | | |
| 0 | 29 | | | 29 | 29 | | |
| 18.8 | 15 | 5 | 7 | 3 | 15 | | |
| 28.1 | 15 | | | | | 11 | 4 |
| 37.5 | 10 | | | | | 1 | 9 |
| 75 | 10 | | | | | 6 | 4 |
| 150 | 10 | | | | | 3 | 7 |

N = Sample size, i.e. the number of volunteers.

TABLE 3

Effect on human red blood cell aggregation within 30 minutes of contrast media comprising iohexol (300 mg I/ml) and 0 to 150 mM/liter sodium ions (added as sodium chloride).

| Na ion concentration (mM/l) | N | Aggregates | | | | Rouleaux | All cells separate |
|---|---|---|---|---|---|---|---|
| | | a | b | c | Total | | |
| 0 | 10 | 5 | 3 | | 8 | 2 | 2 |
| 18.8 | 15 | 3 | 7 | | 10 | 3 | 2 |
| 28.1 | 15 | | | | | 13 | 2 |
| 37.5 | 10 | | | | | 7 | 3 |
| 75 | 10 | | | | | 8 | 2 |
| 150 | 10 | | | | | 9 | 1 |

N = Sample size, i.e. the number of volunteers

From the Tables above, it is clear that Rouleaux formation is maximized at about 28.1 mM/liter sodium.

EXAMPLE 1

Contrast Medium

Composition:
Iohexol* (300 mg I/ml)
Sodium Chloride to 28 mM Na+/liter.
Solid sodium chloride is dissolved in iohexol to produce the desired sodium ion concentration. *Iohexol is available from Nycomed AS under the trade name OMNIPAQUE.

EXAMPLE 2

Contrast Medium

Composition:
Iopentol (350 mg I/ml—from Nycomed AS)
Distilled Water
Sodium chloride solution of 32 mM Na+/liter.
Iopentol (350 mg I/ml) is diluted with distilled water to 280 mg I/ml whereafter sodium chloride, dissolved in distilled water, is added to bring the iodine concentration to 200 mg I/ml and the sodium ion concentration to 32 mM na+/liter.

EXAMPLE 3

Contrast Medium

Composition:
Iohexol (300 mg I/ml)
Sodium chloride solution to 150 mg I/ml and 26 mM Na+/liter.
Iohexol, available as OMNIPAQUE, is diluted with a solution of sodium chloride in distilled water to an iodine concentration of 150 mg I/ml and a sodium concentration of 26 mM/liter.

EXAMPLE 4

Contrast Medium

Composition:
Ioversol (300 mg I/ml)
Sodium chloride as 28 mM/liter
Sodium chloride is dissolved in Ioversol (available from Mallinckrodt, Inc.) to a concentration of 28 mM/l.

I claim:
1. A contrast medium comprising a non-ionic contrast agent in a physiologically tolerable aqueous carrier medium characterized in that said medium has a sodium ion concentration of from 26 up to 36 mM, whereby a beneficial balance between the lowering of red blood cell aggregate formation, lowering of echinocyte formation, increasing of rouleaux formation, lowering of contractile force reduction and lowering of the occurrence of ventricular fibrillation is achieved.

2. A medium as claimed in claim 1 wherein said sodium ion concentration is in the range 27 to 30 mM.

3. A medium as claimed in claim 1 wherein the contrast agent is a ratio 3 or 6 iodinated X-ray contrast agent.

4. A medium as claimed in claim 3 wherein the contrast agent is an iodinated X-ray contrast agent selected from the group consisting of metrizamide, iopromide, iopentol, iopamidol, iohexol, Ioversol, iotrolan and iodixanol.

5. A medium as claimed in claim 3 wherein the contrast agent is present at a concentration of at least 100 mg I/ml.

6. A medium as claimed in claim 1 having an osmolality of less than 1 osm/kg $H_2O$.

7. A medium as claimed in claim 1 further comprising physiologically tolerable cations.

8. A method of cardiac imaging of the human or non-human animal body, which method comprises administering to said body a contrast medium as claimed in claim 1 and generating an image of at least a part of the cardiac region of said body.

9. A medium as claimed in claim 1 wherein said agent is an iodinated X-ray contrast agent.

10. A medium as claimed in claim 7 wherein said cations are selected from the group consisting of chloride, phosphate, hydrogen carbonate and a mixture thereof.

* * * * *

REEXAMINATION CERTIFICATE (4014th)

United States Patent [19]
Almen et al.

[11] B1 5,366,722
[45] Certificate Issued Mar. 14, 2000

[54] CONTRAST MEDIA COMPRISING A NON-IONIC CONTRAST AGENT AND SODIUM IONS

[75] Inventors: Torsten Almen, Malmo; Laars Bååth, Malmö, both of Sweden; Audun Oksendal, Oslo, Norway

[73] Assignee: Nycomed AS, Oslo, Norway

Reexamination Request:
No. 90/005,305, Mar. 25, 1999

Reexamination Certificate for:
Patent No.: 5,366,722
Issued: Nov. 22, 1994
Appl. No.: 08/156,998
Filed: Nov. 24, 1993

[22] PCT Filed: Mar. 9, 1990
[86] PCT No.: PCT/EP90/00393
§ 371 Date: Sep. 24, 1991
§ 102(e) Date: Sep. 24, 1991
[87] PCT Pub. No.: WO90/11094
PCT Pub. Date: Oct. 4, 1990

Related U.S. Application Data

[63] Continuation of application No. 07/761,738, Sep. 24, 1991, abandoned.

[30] Foreign Application Priority Data
Mar. 17, 1989 [GB] United Kingdom .................. 89 06130

[51] Int. Cl.$^7$ ............................. A61B 5/055; A61K 49/04
[52] U.S. Cl. .................. 424/9.43; 424/9.452; 424/9.454; 424/9.455; 424/722; 514/576; 514/922
[58] Field of Search ................................ 424/9.43, 9.452, 424/9.454, 9.455, 722; 514/576, 922

[56] References Cited

U.S. PATENT DOCUMENTS 4,139,605   2/1979   Felder et al. ......................... 424/9.452

FOREIGN PATENT DOCUMENTS 1569242   6/1980   United Kingdom .

*Primary Examiner*—Gary E. Hollinden

[57] ABSTRACT

The invention relates to improved contrast media containing non-ionic contrast agents, e.g. non-ionic iodinated X-ray contrast agents, the improvement being achieved by incorporation of sodium at 20-60 mM/l.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 13–24:

Thus in one aspect, the invention provides a contrast medium comprising a non-ionic contrast agent, preferably an iodinated X-ray contrast agent, in a physiologically tolerable aqueous carrier medium, characterized in that said contrast medium has a sodium ion concentration of from greater than 20 (for example 20.1 or above) to 60 mM/liter, preferably 25 to 40 mM/liter, especially preferably 26 to 36 mM/liter and most especially preferably 27 to 30 mM/liter, with the proviso that where said agent is [loversol] *ioversol* said contrast medium contains sodium ions in the concentration range 26 to 36 mM/liter, preferably 27 to 34 mM/liter.

AS A RESULT OF REEXAMINATION, IT HAS BEEN DETERMINED THAT:

Claims 3 and 9 are cancelled.

Claims 1, 4, 5, 7 and 10 are determined to be patentable as amended.

Claims 2, 6 and 8, dependent on an amended claim, are determined to be patentable.

1. A contrast medium comprising a non-ionic contrast agent in a physiologically tolerable aqueous carrier medium characterised in that said medium has a sodium ion concentration of from 26 up to 36 mM, whereby a beneficial balance between the lowering of red blood cell aggregate formation, lowering of echinocyte formation, increasing of rouleaux formation, lowering of contractile force reduction and lowering of the occurrence of ventricular fibrillation is achieved, *wherein said non-ionic contrast agent is a ratio 3 iodinated X-ray contrast agent, or is a ratio 6 iodinated X-ray contrast agent selected from the group consisting of iotrolan and iodixanol.*

4. A medium as claimed in claim [3] *1* wherein [the] *said non-ionic* contrast agent is an iodinated X-ray contrast agent selected from the group consisting of metrizamide, iopromide, iopentol, iopamidol, iohexol [loversol,] *ioversol,* iotrolan and iodixanol.

5. A medium as claimed in claim [3] *1* wherein the contrast agent is present at a concentration of at least 100 mg I/ml.

7. A medium as claimed in claim 1 further comprising physiologically tolerable [cations] *anions*.

10. A medium as claimed in claim 7 wherein said [cations] *anions* are selected from the group consisting of chloride, phosphate, hydrogen carbonate and a mixture thereof.

* * * * *